United States Patent [19]

Watanabe et al.

[11] Patent Number: 5,179,014

[45] Date of Patent: Jan. 12, 1993

[54] PROCESS FOR THE PREPARATION OF AMIDES USING MICROORGANISMS

[75] Inventors: Ichiro Watanabe; Masami Okumura, both of Kanagawa, Japan

[73] Assignee: Nitto Chemical Industry Co., Ltd., Tokyo, Japan

[21] Appl. No.: 523,287

[22] Filed: May 14, 1990

Related U.S. Application Data

[63] Continuation of Ser. No. 817,185, Jan. 8, 1986, abandoned.

[30] Foreign Application Priority Data

Jan. 8, 1985 [JP] Japan ..................... 60-452

[51] Int. Cl.⁵ ............... C12P 13/02; C12P 13/00; C12P 1/04
[52] U.S. Cl. .................. 435/129; 435/128; 435/170; 435/872
[58] Field of Search ............. 435/128, 129, 170, 813, 435/822, 840, 843, 872, 830

[56] References Cited

U.S. PATENT DOCUMENTS

| | | | |
|---|---|---|---|
| 4,001,081 | 1/1977 | Commeyras et al. | 435/129 |
| 4,248,968 | 2/1981 | Watanabe | 435/129 |
| 4,629,700 | 12/1986 | Prevatt et al. | 435/128 |

FOREIGN PATENT DOCUMENTS

| | | |
|---|---|---|
| 178106 | 4/1986 | European Pat. Off. . |
| 204555 | 12/1986 | European Pat. Off. . |
| 8201992 | 11/1983 | Japan ................ 435/129 |
| 8209987 | 12/1983 | Japan ................ 435/129 |
| 2018240 | 10/1979 | United Kingdom . |

OTHER PUBLICATIONS

*ATCC Catalog of Bacteria,* 16th ed., 1985.
Goodfellow et al, "The Biology of Actinomycetes" Academic Press 1984 pp. 28–29, 40–41, 74–79 and 91–92, 210–211.
Chem. Abs. 101:215828r.
Asano et al, *Agri. Biol. Chem. 46(5):1165–1174 (1982).*

*Primary Examiner*—Irene Marx
*Attorney, Agent, or Firm*—Sughrue, Mion, Zinn, Macpeak & Seas

[57] ABSTRACT

A process for the production of amides utilizing microorganisms is described, which comprises subjecting nitriles having from 2 to 6 carbon atoms to the action of a microorganism belonging to the genus Rhodococcus, and genus Arthrobacter or the genus Microbacterium having an ability to hydrate the nitriles to form the corresponding amides in an aqueous medium.

13 Claims, No Drawings

PROCESS FOR THE PREPARATION OF AMIDES USING MICROORGANISMS

This is a continuation of application Ser. No. 06/817,185 filed Jan. 8, 1986 now abandoned.

FIELD OF THE INVENTION

The present invention relates to a process for the preparation of amides using microorganisms. More particularly, it is concerned with a process for hydrating nitriles by the action of microorganisms, to thereby prepare the corresponding amides.

BACKGROUND OF THE INVENTION

In recent years, extensive investigations have been increasingly made on utilization of microorganisms and enzymes as catalysts for various productions of chemical substances.

An enzyme capable of hydrating nitriles to form the corresponding amides is known as nitrilase or nitrilehydratase. It has been described that bacteria belonging to the genus Bacillus, the genus Bacteridium in the sense of Prevot, the genus Micrococcus and the genus Brevibacterium (Japanese patent application (OPI) No. 86186/76 (corresponding to U.S. Pat. No. 4,001,081) (the term "OPI" as used herein refers to a "published unexamined Japanese patent application")), bacteria belonging to the genus Corynebacterium and the genus Norcardia (Japanese Patent Publication No. 17918/81, corresponding to U.S. Pat. No. 4,248,968), and bacteria belonging to the genus Pseudomonas (Japanese Patent Publication No. 37951/84) have nitrilase activity and hydrate nitriles to form the corresponding amides, particularly acrylonitrile, to form acrylamide.

SUMMARY OF THE INVENTION

The present invention is directed to a process for preparing an amide compound using microorganisms, which comprises subjecting a nitrile having from 2 to 6 carbon atoms to the action of bacteria belonging to the genus Rhodococcus, the genus Arthrobacter, or the genus Microbacterium having an activity to hydrate the nitriles to form the corresponding amides in an aqueous medium.

DETAILED DESCRIPTION OF THE INVENTION

The process of the present invention is particularly effective in the preparation of acrylamide from acrylonitrile.

The microorganisms used according to the present invention are bacteria having nitrilase activity belonging to the genus Rhodococcus, the genus Arthrobacter, and the genus Microbacterium. Typical examples are Rhodococcus sp. S-6 FERM BP-687, *Rhodococcus erythropolis* IFM 155, *Rhodococcus rhodochrous* IFM 153, *Arthrobacter oxydans* IFO 12138, *Arthrobacter aurescens* IAM 12340, and *Microbacterium flavum* IAM 1642.

Bacteria designated by the symbols IFM, IFO, and IAM are known microorganisms and are readily available through The Japanese Federation of Culture Collections of Microorganisms (JFCC) of The Research Institute for Chemobiodynamics, Chiba University (IFM); The Institute for Fermentation, Osaka (IFO); and Institute of Applied Microbiology, University of Tokyo (IAM), respectively. Rhodococcus sp. S-6 is a strain isolated by the present inventors, having particularly high nitrilase activity, and has been deposited in the Fermentation Research Institute, Agency of Industrial Science & Technology, Ministry of International Trade and Industry, Japan, as FERM-BP No. 687. Bacteriological characteristics of the strain are shown below. Rhodococcus sp. S-6

(a) Morphology
  (1) Small rod-shaped, 0.5–0.8 $\mu$m diameter $\times$ 1–5 $\mu$m length
  (2) At an initial stage of cultivation, the cell is in a long rod-shaped form and irregular branches are observed. Later it breaks and splits into a spherical or short rod-shaped form (pleomorphism).
  (3) Motility: none
  (4) Formation of spore: none
  (5) Gram staining: positive (+)
  (6) Acid fastness: negative (−)

(b) Growth state in various culture media (30° C.)
  (1) Bouillon agar plate culture: colonies are circular, irregular, smooth in surface, and colored slightly pink.
  (2) Bouillon agar slant culture: good growth, trapezoidal in cross section, no luster, and slightly pink.
  (3) Bouillon liquid culture: vigorous growth while forming a pellicle, and the liquid is transparent and precipitates with growth.

(c) Physiological characteristics
  (1) Reduction of nitrate: positive (+)
  (2) Decomposition of urea: positive (+)
  (3) Indole production: negative (−)
  (4) Hydrolysis of starch: negative (−)
  (5) Decomposition of gelatin: negative (−)
  (6) Decomposition of cellulose: negative (−)
  (7) Oxidase: negative (−)
  (8) Catalase: positive (+)
  (9) Requirement of a free oxygen: positive (+)
  (10) Growth in anaerobic condition: negative (−)
  (11) O/F test: 0
  (12) Growth at 37° C.: positive (+)
  (13) Requirement of vitamins: negative (−)
  (14) Production of gas from glucose: negative (−)
  (15) Production of acid from glucose: positive (+)

(d) Chemical composition of cells
  (1) Contains meso-diaminopimelic acid, arabinose and galactose (B. Becker et al., *Applied Microbiology*, Vol. 12, p. 421 (1964), and H. A. Lechevalier et al., *The Actinomycetales*, p. 311 (1970)).
  (2) Contains fatty acids of $C_{16}$ (n, $F_1$), $C_{18}$ ($F_1$) and $C_{19}$ (10-$CH_3$) as main fatty acids (K. Komagata et al., *International Journals of Systematic Bacteriology*, Vol. 33 (2), p. 188 (1983)).
  (3) Contains $C_{32}$–$C_{46}$ mycolic acids as the mycolic acid type (M. Goodfellow, *Microbiological Classification and Identification*, (1980)).

Referring to *Bergey's Manual of Determinative Bacteriology*, H. Ans-G. Schlegel, *The Prokaryotes*, Vol. II (1981), and the literature described in (d) concerning chemical classification of microorganisms, the strain S-6 is determined such that it is a bacillus which is gram-positive, negative in formation of spore, aerobic, has polymorpholis, and is negative in acid fastness. This strain contains therein meso-diaminopimelic acid, arabinose and galactose, $C_{16}$ (n, $F_1$), $C_{18}$ ($F_1$) and $C_{19}$ (10-$CH_3$) as fatty acid types of acids, and $C_{32}$–$C_{46}$ mycolic acids as the mycolic acid type.

Based on the above bacteriological characteristics, the present strain is identified as a bacterium belonging to the genus Rhodococcus.

In cultivation of microorganisms as used herein, an ordinary culture medium containing a carbon source (e.g., glucose, glycerol, and maltose), a nitrogen source (e.g., ammonium sulfate and ammonium chloride), an organic nutrient source (e.g., yeast extract, peptone, meat extract, soybean protein hydrolyzate, and corn steep liquor (CSL)), an inorganic nutrient source (e.g., phosphate, magnesium, potassium, zinc, iron, and manganese), and so forth is used. This cultivation is aerobically carried out with stirring at a pH value of from 6 to 8 and at a temperature of from 20° to 35° C., and preferably 25° to 30° C., for from 1 to 3 days.

In the practice of the process of the present invention, one strain selected from the above microorganisms is cultured for 2 to 3 days according to the above-described method, and the resulting cultures or cells separated from the cultures, or treated cells (crude enzymes, immobilized cells, etc.) are suspended in water, a buffer or physiological saline water and then a nitrile compound is added thereto.

The nitrile compound is acted on by cells by reacting an aqueous medium generally containing from about 0.01 to 10 wt % of the cells and from about 0.1 to 10 wt % of the nitrile compound at a temperature of from the freezing point thereof to 30° C., and preferably the freezing point to 15° C., at a pH of from 6 to 10, and preferably from 7 to 9, for a period of from 0.5 to 10 hours.

Nitrile compounds used as a substrate are biologically very toxic, and exert serious adverse influences on the present enzymatic reaction. For this reason, the nitrile compound is gradually added in a controlled manner such that the concentration of nitriles in the system is preferably not more than 5 wt %, and more preferably not more than 2 wt %.

If the pH value is outside the above-defined range, the amide formed and accumulated is further hydrolyzed, and the stability of the cells is reduced. Thus, it is preferred to control the pH value within the range of from 7 to 9 by gradually adding caustic alkali (e.g., NaOH and KOH), or by previously adding a buffer to the system.

If reaction conditions are appropriately controlled, the desired amide can be formed and accumulated from the nitrile compound at a conversion value of nearly 100%, and with substantially no formation of by-products.

The amide thus formed can be recovered from the reaction mixture by commonly known techniques. For example, cells are separated from the reaction mixture by techniques such as centrifugal separation, treated with activated carbon, an ion exchange resin or the like, to remove colored substances, impurities and the like, and then concentrated under reduced pressure to yield the desired amide, for example, acrylamide.

The present invention is described in greater detail with reference to the following examples. All parts and percents are by weight.

The various nitriles and their corresponding amides were quantitatively analyzed by gas chromatography, and their corresponding organic acids by high performance liquid chromatography.

EXAMPLE 1

A strain, Rhodococcus sp. S-6, was aerobically cultured on a medium (pH: 7.2) containing 1% of glucose, 0.5% of peptone, 0.3% of yeast extract, and 0.3% of meat extract at 30° C. for 48 hours. The cells thus formed were removed by centrifugal separation and washed with a 0.05M phosphate buffer (pH: 7.7). This procedure was repeated to prepare washed cells of the S-6 strain (water content: 80%).

A mixture of 0.5 part of the washed cells and 84.5 parts of a 0.05M phosphate buffer (pH: 8.5) was prepared, and then 15 parts of acrylonitrile was intermittently added with stirring at from 0° to 3° C. while controlling conditions such that the concentration of acrylonitrile in the reaction system did not exceed 2%, to thereby subject the acrylonitrile to a hydration reaction. Addition of acrylonitrile was completed in about 3 hours. To ensure the completion of the reaction, stirring was further continued for several hours. Then, cells were removed by centrifugal separation to yield a clear solution. This solution contained 20% of acrylamide, and the yield of acrylamide was more than 99.9%. Unreacted acrylonitrile was not detected at all, and the proportion of by-produced acrylic acid was not more than 0.1% (based on the weight of the acrylamide).

Water was distilled off from the clear solution at a temperature of not more than 50° C.; the clear solution was concentrated to precipitate crystals. These crystals were recrystallized from methanol to yield colorless plate-shaped crystals. This compound was identified as acrylamide based on melting point, elementary analysis, and IR.

EXAMPLE 2

Washed cells of the S-6 strain were obtained in the same manner as in Example 1 and measured for their reactivity to various nitriles under the following conditions.

| (a) Reaction Conditions | |
| --- | --- |
| Nitrile Compound | 2.5% |
| Potassium Phosphate Buffer | pH 7.7/0.05M |
| Cells (as dry cells) | 5 mg |
| Temperature | 10° C. |
| Reaction Time | 10 min |
| Amount of the Reaction Solution | 10 ml |
| (b) Reaction Results | |
| Type of Nitrile | Amide-Forming Activity* |
| Acetonitrile | 30 |
| Propionitrile | 102 |
| Acrylonitrile | 100 |
| Methacrylonitrile | 123 |
| Butyronitrile | 51 |
| Valeronitrile | 11 |
| Nicotinonitrile | 16 |

*Relative value indicated with the activity to acrylonitrile as 100.

EXAMPLE 3

100 ml of a culture medium comprising 1% of glycerol, 0.1% of $KH_2PO_4$, 0.05% of $MgSO_4.7H_2O$, 0.001% of $FeSO_4.7H_2O$, 0.5% of soybean protein hydrolyzate, and 0.1% of yeast extract (pH: 7.5) which had been sterilized and to which 0.5% of sterile isobutyronitrile had been added was prepared in 500 ml of an Erlenmeyer flask. Then, 1 ml of a culture of a type of culture strain as shown below which had been cultured for 48 hours in the same culture medium as in Example 1 was added, and cultured with vibration at 25° C. for 48 hours. After the cultivation was completed, cells were recovered by centrifugal separation and then washed with a 0.05M phosphate buffer (pH: 7.7). This procedure was repeated to yield washed cells. These cells were measured for activity of formation of acrylamide from acrylonitrile in the same manner as in Example 2.
The results are shown in Table 1.

TABLE 1

| Type of Strain | Acrylamide-Forming Activity ($\mu M/mg \cdot hr$) |
| --- | --- |
| Rhodococcus erythropolis IFM 155 | 3.5 |
| Rhodococcus rhodochrous IFM 153 | 2.5 |
| Arthrobacter oxydans IFO 12138 | 5.0 |
| Arthrobacter aurescens IAM 12340 | 2.0 |
| Microbacterium flavum IAM 1642 | 2.0 |

While the invention has been described in detail and with reference to specific embodiments thereof, it will be apparent to one skilled in the art that various changes and modifications can be made therein without departing from the spirit and scope thereof.

What is claimed is:

1. A process for producing an amide compound utilizing microorganism, which comprises subjecting a nitrile to the action of the bacteria Rhodococcus S-6 having an ability to hydrate the nitrile to form the corresponding amide compound in an aqueous medium, wherein the nitrile is selected from the group consisting of acetonitrile, propionitrile, acrylonitrile, methacrylonitrile, butyronitrile, isobutyronitrile, valeronitrile, and nicotinonitrile, and recovering the amide compound from the aqueous medium.

2. A process as in claim 1, wherein the aqueous medium is maintained at a temperature of from the freezing point thereof to 30° C.

3. A process as in claim 1, wherein the aqueous medium is maintained at a temperature of from the freezing point thereof to 15° C.

4. A process as in claim 1, wherein the aqueous medium is maintained at a pH of from 6 to 10.

5. A process as in claim 1, wherein the aqueous medium is maintained at a pH of from 7 to 9.

6. A process as in claim 1, wherein the nitrile is continuously or intermittently added to the aqueous medium such that the concentration of the nitrile is not more than 5 wt %.

7. A process as in claim 1, wherein the nitrile is continuously or intermittently added to the aqueous medium such that the concentration of the nitrile is not more than 2 wt %.

8. A process as in claim 1, wherein the nitrile is acrylonitrile.

9. A process as in claim 1, wherein the nitrile is acetonitrile.

10. A process as in claim 1, wherein the nitrile is propionitrile or acrylonitrile.

11. A process as in claim 1, wherein the nitrile is methacrylonitrile, butyronitrile or isobutyronitrile.

12. A process as in claim 1, wherein the nitrile is valeronitrile.

13. A process as in claim 1, wherein the nitrile is nicotinonitrile.

* * * * *